(12) United States Patent
Davis (10) Patent No.: US 9,415,082 B1
(45) Date of Patent: Aug. 16, 2016

(54) COMPOSITIONS AND METHODS FOR TOPICALLY TREATING SKIN CONDITIONS IN MAMMALS

(71) Applicant: Leslie Elice Davis, Ricewood, TX (US)

(72) Inventor: Leslie Elice Davis, Ricewood, TX (US)

( * ) Notice: Subject to any disclaimer, the term of this patent is extended or adjusted under 35 U.S.C. 154(b) by 0 days.

(21) Appl. No.: 14/850,180

(22) Filed: Sep. 10, 2015

Related U.S. Application Data (60) Provisional application No. 62/048,892, filed on Sep. 11, 2014.

(51) Int. Cl.

| A61K 36/28 | (2006.01) |
|---|---|
| A61K 36/889 | (2006.01) |
| A61K 9/00 | (2006.01) |
| A61K 9/06 | (2006.01) |
| A61K 36/185 | (2006.01) |
| A61K 36/736 | (2006.01) |
| A61K 36/47 | (2006.01) |
| A61K 36/61 | (2006.01) |
| A61K 36/53 | (2006.01) |
| A61K 31/355 | (2006.01) |
| A61K 36/87 | (2006.01) |
| A61K 36/63 | (2006.01) |
| A61K 31/231 | (2006.01) |

(52) U.S. Cl.
CPC ............ *A61K 36/28* (2013.01); *A61K 9/0014* (2013.01); *A61K 9/0017* (2013.01); *A61K 9/06* (2013.01); *A61K 31/231* (2013.01); *A61K 31/355* (2013.01); *A61K 36/185* (2013.01); *A61K 36/47* (2013.01); *A61K 36/53* (2013.01); *A61K 36/61* (2013.01); *A61K 36/63* (2013.01); *A61K 36/736* (2013.01); *A61K 36/87* (2013.01); *A61K 36/889* (2013.01)

(58) Field of Classification Search
None
See application file for complete search history.

(56) References Cited

U.S. PATENT DOCUMENTS

| 2008/0234224 A1* | 9/2008 | Kamachi | A61K 8/73 514/54 |
| 2009/0068255 A1* | 3/2009 | Yu | A61K 8/0212 424/450 |
| 2012/0276030 A1* | 11/2012 | Marthaler | A61Q 1/02 424/63 |

* cited by examiner

*Primary Examiner* — Susan Hoffman
(74) *Attorney, Agent, or Firm* — Mitchell A. Rossman; Terra Nova Patent Law, PLLC (57) ABSTRACT

The present invention provides compositions and methods for treating skin conditions in a mammal. The compositions include, for example, *Candelilla* wax; Shea nut butter; Coconut oil; hempseed oil; *Kukui* nut oil; jojoba oil; sweet almond oil; Rosemary extract; Niaouli oil; and Vitamin E acetate. The skin conditions include, for example, a intertrigo, a skin fold, skin fold dermatitis, interdigital dermatitis, facial fold dermatitis, vulvar fold dermatitis, tail fold pyoderma and dermatitis, impetigo, Nasodigital hyperkeratosis, pruritus, pyoderma, pyotraumatic dermatitis, malodor, lesions, dermal rashes, dermal bacterial infection, dermal fungal infection, dermal weeping, hot spots, irritation, chaffing, itching, inflammation, or a combination thereof.

11 Claims, 2 Drawing Sheets

COMPOSITIONS AND METHODS FOR TOPICALLY TREATING SKIN CONDITIONS IN MAMMALS

RELATED APPLICATIONS

This application claims priority to U.S. Provisional Patent Application Ser. No. 62/048,891 filed Sep. 11, 2014, which is hereby incorporated by reference in its entirety for all purposes.

BACKGROUND OF THE INVENTION

Mammals with folds and wrinkles often develop inflammatory skin conditions. Typical mammals include, for example, dogs, cats and humans with loose and wrinkled skin.

What is needed is a composition for treating a wide variety of inflammatory skin conditions.

SUMMARY OF THE INVENTION

The present invention provides compositions and methods for topically treating mammals with skin conditions. The mammals may include, for example, a human, canine, a feline, or a rabbit. The skin condition may include, for example, intertrigo, a skin fold, skin fold dermatitis, interdigital dermatitis, facial fold dermatitis, vulvar fold dermatitis, tail fold dermatitis, pyoderma and dermatitis, impetigo pruritus, pyotraumatic dermatitis, malodor, lesions, dermal rashes, dermal bacterial infection, dermal fungal infection, dermal weeping, irritation, chaffing, itching, inflammation, or a combination thereof. These skin conditions are often found in brachycephalic dogs and obese humans.

The present invention provides a composition for topical treatment of a skin condition in a mammal. This composition includes: about 5 weight percent to about 45 weight percent *Candelilla* wax; about 5 weight percent to about 40 weight percent Shea nut butter oil; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; about 0.1 weight percent to about 10 weight percent grapeseed oil; about 0.1 weight percent to about 10 weight percent olive leaf extract; about 0.1 weight percent to about 10 weight percent *calendula* leaf extract; and about 0.1 weight percent to about 5 weight percent Vitamin E acetate.

The present invention provides a composition for topical treatment of a skin condition in a mammal. This composition includes: about 7 weight percent to about 20 weight percent *Candelilla* wax; about 5 weight percent to about 25 weight percent Shea nut butter; about 5 weight percent to about 30 weight percent Coconut oil; about 5 weight percent to about 25 weight percent hempseed oil; about 5 weight percent to about 25 percent grapeseed oil, about 5 weight percent to about 15-weight percent *Kukui* nut oil; about 5 weight percent to about 15 weight percent jojoba oil; about 5 weight percent to about 15 weight percent sweet almond oil; about 0.1 weight percent to about 5 weight percent Rosemary extract; about 0.1 weight percent to about 5 weight percent Niaouli oil; about 0.1 weight percent to about 10 weight percent grapeseed oil; about 0.1 weight percent to about 10 weight percent olive leaf extract; about 0.1 weight percent to about 10 weight percent *calendula* leaf extract; and about 0.1 weight percent to about 5 weight percent Vitamin E acetate.

The present invention provides a composition for topical treatment of a skin condition in a mammal. This composition includes: about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate.

In one embodiment, the composition includes: about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate.

In one embodiment, the skin condition is a intertrigo, a skin fold, skin fold dermatitis, interdigital dermatitis, facial fold dermatitis, vulvar fold dermatitis, tail fold pyoderma and dermatitis, impetigo, Nasodigital hyperkeratosis, pruritus, pyoderma, pyotraumatic dermatitis, malodor, lesions, dermal rashes, dermal bacterial infection, dermal fungal infection, dermal weeping, hot spots, irritation, chaffing, itching, inflammation, or a combination thereof.

In one embodiment, the skin condition is a skin fold. In one embodiment, the skin condition is skin fold dermatitis. In one embodiment, the mammal includes a human, canine, a feline, or a rabbit. In one embodiment, the human is an obese human. In one embodiment, the canine is a brachycephalic dog. In one embodiment, the brachycephalic dog is an Affenpinscher, an American Bulldog, an American Cocker Spaniel, an American Pit Bull Terrier, an American Staffordshire Terrier, a Bichon Frise, a Boston Terrier, a Boxer, a Brussels Griffon, a Bulldog, a Bullmastiff, a Cane Corso, a Cavalier King Charles Spaniel, a Chihuahua (apple-headed), a Chow Chow, a Dogo Argentino, a Dogue de Bordeaux, a English Mastiff, a French Bulldog, a Japanese Chin, a King Charles Spaniel, a Lhasa Apso, a Maltese, a Neapolitan Mastiff, a Newfoundland, a Pekingese, a Presa Canario, a Pug, a Shar-Pei, a Shih Tzu, a Silky Terrier, a Tibetan Spaniel, a Valley Bulldog, or a Yorkshire Terrier. In one embodiment, the feline is a cat. In one embodiment, the cat is a brachycephalic cat.

In one embodiment, the brachycephalic cat is a British Shorthair, an Exotic Shorthair, a Himalayan cat, a Persian cat, or a Scottish Fold. In one embodiment, the rabbit is a brachycephalic rabbit. In one embodiment, the brachycephalic rabbit is a Jersey Wooly rabbit, a Lionhead rabbit, or a Lop rabbit.

In one embodiment, the composition is a solution, a spray, a lotion, a gel, a cream, a balm, a paste, or an ointment. In one embodiment, the composition is a balm. In one embodiment, the composition is a paste. In one embodiment, the composition is an ointment.

In one embodiment, the composition further includes one or more vitamins, one or more herbs, one or more antimicrobial agents, one or more anti-inflammatory agents, one or more non-steroidal cosmetic soothing agents, one or more skin lightening agents, one or more anti-wrinkle agents, one or more anti-itching agents, one or more antioxidants, one or more fragrances, one or more conditioners, or a combination thereof.

The present invention provides a composition for topical treatment of a skin condition in a mammal. This composition consists essentially of: about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate.

In one embodiment, the composition consists essentially of: about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate.

The present invention also provides a method of topically treating a skin condition of a mammal. The method includes: administering a composition including; about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate, to an area of skin condition of the mammal to be treated.

In one embodiment, the composition includes; about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate.

The present invention also provides a method of topically treating a skin condition of a mammal. The method includes: administering a composition consisting essentially of; about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate to an area of skin condition of the mammal to be treated.

The present invention also provides a method of topically treating a skin condition of a mammal. The method includes: administering a composition consisting essentially of: about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate to an area of skin condition of the mammal to be treated.

The present invention also provides a method of topically treating a skin fold dermatitis in a mammal. The method includes: administering a composition including; about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate to an area of skin condition of the mammal to be treated.

In one embodiment, the composition includes; about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate.

The present invention also provides a method of topically treating skin fold dermatitis in a mammal. The method includes: administering a composition consisting essentially of; about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate to an area of skin condition of the mammal to be treated.

The present invention also provides a method of topically treating a skin fold dermatitis in a mammal. The method includes: administering a composition consisting essentially of: about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; and about 1 weight percent Vitamin E acetate to an area of skin condition of the mammal to be treated.

The present invention also provides a kit for topically treating a skin condition of a mammal. The kit includes: a topical composition including; about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; about 0.1 weight percent to about 10 weight percent Vitamin E acetate; and instructions for using the topical composition and a dosage regime thereto.

The present invention also provides a kit for topically treating a skin condition of a mammal. The kit includes: a topical composition including: about 25 weight percent *Candelilla* wax; about 20 weight percent Shea nut butter; about 15 weight percent Coconut oil; about 10 weight percent hempseed oil; about 10 weight percent *Kukui* nut oil; about 10 weight percent jojoba oil; about 10 weight percent sweet almond oil; about 1 weight percent Rosemary extract; about 1 weight percent Niaouli oil; about 1 weight percent Vitamin E acetate; and instructions for using the topical composition and a dosage regime thereto.

The present invention provides a composition for topical treatment of a skin condition in a mammal. The composition includes: about 1 weight percent to about 20 weight percent hempseed oil; about 5 weight percent to about 40 weight percent Shea butter oil; about 1 weight percent to about 20 weight percent *Kukui* oil; about 1 weight percent to about 20 weight percent jojoba oil; about 1 weight percent to about 20 weight sweet almond oil; about 1 weight percent to about 45 weight *Aloe Vera*; about 1 weight percent to about 45 weight *Calendula* oil; about 1 weight percent to about 20 weight tea tree oil; and about 1 weight percent to about 45 weight *Candelilla* wax.

BRIEF DESCRIPTION OF THE DRAWINGS

Embodiments of the invention may be best understood by referring to the following description and accompanying drawings, which illustrate such embodiments. In the drawings.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention provides compositions and methods for topically treating mammals with skin conditions. The mammals may include, for example, a human, canine, a feline, or a rabbit. The skin condition may include, for example, intertrigo, a skin fold, skin fold dermatitis, interdigital dermatitis, facial fold dermatitis, vulvar fold dermatitis, tail fold pyoderma and dermatitis, impetigo, Nasodigital hyperkeratosis, pruritus, pyoderma, pyotraumatic dermatitis, malodor, lesions, dermal rashes, dermal bacterial infection, dermal fungal infection, dermal weeping, hot spots, irritation, chaffing, itching, inflammation, or a combination thereof. These skin conditions are often found in brachycephalic dogs and obese humans.

The present invention also provides unparalleled activity in topical management of pyoderman and *Malassezia*. It can be used for the antiseptic cleaning of interdigital areas, nasal lip, and other fold pyodermas in cats and dogs.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *The American Heritage Dictionary of the English Language*, Houghton Mifflin, Boston Mass., 1981.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "administration" refers to a method of placing a composition in a desired site.

As used herein, the term "brachycephalic" refers to a short-headed or broad-headed mammal with a cephalic index of over 80.

As used herein, the term "dermis" refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

As used herein, the terms "include," "for example," "such as," and the like are used illustratively and are not intended to limit the present invention.

As used herein, the term "impetigo" refers to Puppy Pyoderma.

As used herein, the term "patient" refers to a warm-blooded animal, and preferably a mammal, for example, a cat, dog, horse, cow, pig, mouse, rat, or primate, including a human.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacoepia* describe the analytical criteria to assess the pharmaceutical acceptability of numerous ingredients of interest.

As used herein, the term "pruritus" refers to a localized or generalized itching due to irritation of sensory nerve endings from organic or psychogenic causes.

As used herein, the term "pyoderma" refers to an inflammatory skin disease caused by pus-forming micro-organisms (e.g., *staphylococci*) and marked by pus-forming legions.

As used herein, the term "pyotraumatic dermatitis" or "hot spots" refers to self-induced skin lesionsthat are usually caused (and made worse) by biting, licking, constant chewing or scratching. This inflammation manifests as any or all of the following: redness, oozing, hair loss, and pus. This condition usually appears suddenly, and is a "vicious cycle" type of problem: an inciting factor for causing the animal to scratch and bite (skin irritation, parasites, etc.), continual licking, scratching and biting, and finally normal skin surface bacteria multiplying, causing the dermatitis (skin infection) that causes more licking, chewing, and scratching.

As used herein, the term "skin" refers to the external tissue layer in humans and animals consisting of epidermis and dermis.

As used herein, the term "skin fold" refers to a fold in the external tissue layer in humans and animals consisting of epidermis and dermis.

As used herein, the term "skin fold dermatitis" refers to an inflammation in a fold in the external tissue layer in humans and animals consisting of epidermis and dermis.

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to either "treatment" or "prevention," thus, agents that either treat damage or prevent damage are "therapeutic."

As used herein, the phrase "therapeutic kit" refers to a collection of components that can be used in a medical treatment.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells, which line hollow organs or body cavities).

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

Main Ingredients

Hempseed oil: Hempseed oil is a natural oil that can be obtained by cold pressing hemp seeds, which are seeds from the plant species *Cannabis sativa*. The oil from these seeds contains a mixture of natural fats (triesters of glycerol, also known as triglycerides). Hempseed oil is an anti-inflammatory, an anti-oxidant, and high in essential fatty acids. It is a non-greasy, emollient and moisturizing compound with excellent moisture balancing properties. Hemp seed oil contains a high amount of polyunsaturated essential fatty acids-57% linoleic (LA) and 19% linolenic (LNA) acids. Hemps seed oil also contains antioxidants in the form of Vitamin E acetate and carotene. Adding to that, phytosterols, phospholipids, as well as a number of minerals, including calcium, magnesium, sulfur, potassium and phosphorus are also found in the oil. Hemp seed oil is reputed to have a higher percentage of polyunsaturated fats than any other vegetable oil. Hemp seed oil is very high in both Omega-3 and Omega-6 essential fatty acids (EFAs), which are both potent antioxidants and prostaglandin-mediating anti-inflammatories. Hemp seed oil has the lowest amount of saturated fatty acids and the highest amount of the polyunsaturated essential fatty acids of all oils. Flax seed oil comes in second. EFA's are involved in producing life energy from food and the movement of that energy throughout the body. EFAs govern growth, vitality and state of mind. Linoleic acid and linolenic acid are precursors to the prostaglandins, a short-lived hormone-like family of substances that regulate many functions in all tissues.

Shea nut butter: Shea nut butter is a natural butter extracted from the nuts of the Shea tree by traditional techniques, i.e., using water as an extraction solvent, or using other solvents such as, for example, ethanol or hexane. Shea nut butter is known for its properties as a moisturizer and emollient and as an anti-inflammatory agent. Shea nut butter is anti-inflammatory, restores skin's natural elasticity, and is a natural sunscreen, an emollient, and a moisturizer. It is rich in antioxidants like tocopherols & catechins, contains stearic & oleic acids, which promotes & protects skin barrier health, contains triterpene alcohols, known to reduce inflammation, cinnamic acid esters, which have a limited capacity to absorb UV radiation, and lupeol, which prevents the effects of skin aging by blocking the action or function of enzymes that degrade skin proteins.

*Kukui* nut oil: *Kukui* nut tree is a native tree in all countries from western Polynesia to southern Asia and is generally found in woods of lower mountain zone, web gushes and valleys, ravines and hanging valleys of tropics and subtropics. In the United States, the *Kukui* tree is found in all islands of Hawaii. Certain medicinal and other uses of various portions of the *Kukui* nut tree or its nut have been reported, particularly in native Hawaiian medicine, the *Kukui* nut has many uses.

Jojoba Oil: Jojoba oil is a liquid wax ester derived from a desert plant that grows in the southwestern United States. It closely resembles the esters produced by the skin (known as sebum). This gives jojoba oil a natural affinity with the skin, making it readily absorbable without leaving a greasy or tacky residue on the skin. Jojoba oil is also excellent for hair and scalp conditioning. It has anti-inflammatory and antibacterial properties, as well as antioxidant properties that prevent it from turning rancid like other oils.

Sweet Almond Oil: Sweet almond oil is a nutrient for skin conditioning with glucosides, vitamins, and minerals, and aids with eczema and itchy, dry, and inflamed skin. Sweet almond oil nourishes hair and soothes hair cuticles, making the user's hair longer and thicker, adding shine to the hair, and controlling hair fall.

*Candelilla* wax: *Candelilla* wax is a wax derived from the leaves of the small *Candelilla* shrub native to northern Mexico and the southwestern United States, *Euphorbia cerifera* and *Euphorbia antisyphilitica*, from the family Euphorbiaceae. It is yellowish-brown, hard, brittle, aromatic, and opaque to translucent. With a melting point of 68.5-72.5° C., *candelilla* wax consists of mainly hydrocarbons (about 50%, chains with 29-33 carbons), esters of higher molecular weight (20-29%), free acids (7-9%), and resins (12-14%, mainly triterpenoid esters). The high hydrocarbon content distinguishes this wax from carnauba wax. It is insoluble in water, but soluble in many organic solvents such as acetone, chloroform, benzene. Because of its high ester, fatty acid and moisture retaining properties, *Candelilla* wax is one of the best suited ingredients for increasing the protective coating of the present invention.

*Kukui* Nut Oil: *Kukui* nut oil, extracted from the nuts of *Kukui* nut trees, has been used for hundreds of years by native Hawaiians to treat a variety of ailments. Of particular note is the application to skin disorders. The rapid penetration of the oil into the skin has been shown to bring rapid, soothing relief for superficial burns, chapped skin, and minor skin diseases. Application prior to exposure of the skin to challenges such as wind and sun also help prevent skin damage from occurring. The inclusion of *Kukui* nut oil acts in synergy as an adjunct to the therapeutic agent to promote the alleviation of the medical condition being treated. The results of these combinations against inflamed, infected, or other skin disorders are more effective than each of the components, the *Kukui* nut oil, on the one hand, or active dermopharmaceutical agents, on the other hand, when the latter are taken separately, at comparable concentrations.

Vitamin E acetate: Vitamin E acetate refers to DL-Alpha tocopheryl acetate, or CAS No. 7695-91-2; 58-95-7, which is man-made modified artificial version of Vitamin E. Vitamin E acetate is available from Lotioncrafter® LLC., 48 Hope Lane, East Sound, Wash. 98245.

Niaouli Oil: Niaouli oil is an essential oil obtained by steam distillation from the fresh leaves of *Melaleuca viridiflora*, the main components of which are 1, 8-cineole, α-terpineol, α-pinene and limonene. Such essence is also known commercially as gomenol, and is used in the disorders of the upper respiratory tract, as a balsamic and expectorant agent and, above all, as an anti-infective agent.

Coconut Oil: Coconut oil is a fat consisting of about 90% saturated fat. The contains predominantly medium chain triglycerides; with roughly 92% saturated fatty acids, 6% monounsaturated fatty acids and 2% polyunsaturated fatty acids. Of the saturated fatty acids, coconut oil is primarily 44.6% lauric acid, 16.8% myristic acid, 8.2% palmitic acid and 8% caprylic acid, although it contains seven different saturated fatty acids in total. Its only monosaturated fatty acid is oleic acid while its only polyunsaturated fatty acid is linoleic acid. Unrefined coconut oil melts at 24-25° C. (76° F.) and smokes at 170° C. (350° F.) while refined coconut oil has a higher smoke point of 232° C.

Rosemary Extract: Rosemary extract is a generic term describing a number of different chemical compositions that may contain several different active components. Among the common components that are found in rosemary extract are camosol, carnosic acid, methoxy carnosic acid, rosmarinic acid, rosmanol and rosmaridiphenol, in different proportions depending on the individual extract. Rosemary extract is a potent antioxidant and anti-inflammatory that strengthens capillaries and protects against free radical damage (oxidation) to DNA. Rosmarol, an extract from the leaves, has shown remarkably high antioxidant activity.

*Calendula* $CO_2$ extract: Regenerative, antioxidant, antiinflammatory, wound healing, from about 0.5 to about 10 weight percent.

Olive Leaf Extract: from about 0.5 to about 15 weight percent.

Optional Ingredients

Other ingredients that may be used in this formulation may include, for example, an effective amount of an added preservative, which may be man-made.

Other ingredients that may be used in this formulation may include, for example, oils such as Abyssinian Oil, Apricot Kernel Oil, Argan Oil, Avena Oat Oil, Avocado Oil, Boabab Oil, Black Cumin Seed Oil, Black Current Oil, Blueberry Seed Oil, Borage Seed Oil, Camelina Oil, Castor Oil, Evening Primerose Oil, Hazelnut Oil, Olive Oil, Macadamia Nut Oil, Manila Oil, Meadowfoam Seed Oil, Neem Oil, Palm Fruit Oil, Palm Kernel Oil, Peach Kernel Oil, Pomegranate Seed Oil, Passionfruit Oil, Pumpkin Seed Oil, Rice Bran Oil, Rosehip Seed Oil, Safflower Oil, Sea Buckthorn Oil, Soybean Oil, Sunflower Seed Oil, Tamanu Oil, Wheat Germ Oil, and the like; butters such as Cocoa butter, Kokum Butter, Cupuacu Butter, Illipe butter, Mango Butter, and the like; waxes such as Beeswax, Sunflower wax, Carnauba Wax, and Emulsifying Wax; plant extracts such as *Arnica, Calendula*, Carrot Seed, Mullein, Comfrey, Plantain, Marshmallow Root, Slippery Elm, and the like; Essential oils such Benzoin Resin, Bergamot, Cajeput, Camphor, Carrot Seed, Catnip, Chamomile, Blue, Chamomile, Roman, Chamomile, Moroccan, Clary Sage, Clove Bud, Copaiba Balsam, *Eucalyptus*, Frankincense, Galbanum, Geranium, Helichrysum, Lavender, Melissa, Lemongrass, Manuka, Myrrh, Oregano, Palmarosa, Peppermint, Peru Balsam, Ravensara, Rosemary, Sage, Sandalwood, Spikenard, St. John's Wort, Tea Tree, Valerian, Vetiver, Yarrow, Ylang Ylang, and the like.

In one embodiment of the present invention, the composition may be applied on the surface of the affected skin area in adequate quantity and in the manner conventional in the relevant field. The topical composition may be in a solid, semi-solid, or liquid form. Suitable solid topical compositions include, for example, sticks or bars similar to deodorant sticks, aluminum tins, or glass jars. Suitable semi-solid mixtures topical compositions may include, for example, gels, lotions, pastes, balms, creams, salves and ointments. Suitable liquid topical compositions include, for example, body or face washes, rinses, solutions for a wipe, and sprays.

A person skilled in the art can select both the appropriate presentation form and the method for preparing it on the basis of his general knowledge, taking into account on the one hand the nature of the constituents used, and on the other hand the intended use of the composition. The compositions may be prepared by any method known and practiced in the art. For example, U.S. Pat. Nos. 4,883,664; 4,246,285; 4,847,068; 6,927,205; 5,824,323; 5,143,940; 6,030,931; and 7,186,416, disclose various skin care compositions in the form of salves, lotions, creams, solutions, gels, foams and solids. In addition, various solid formulations of gel stick compositions are disclosed, for example, in U.S. Pat. Nos. 4,518,582; 4,719,102; and 4,722,835.

The composition for the topical treatment of a brachycephalic skin condition in a mammal may also include one or more optional ingredients, for example, anti-viral agents, palliative agents, anti-itch agents, anti-microbial and anti-fungal agents, non-steroid cosmetic soothing agents, steroids, skin conditioning agents, emollients, humectants, odorants, preservatives, solvents, thickening, stiffening and suspending agents, other agents, and combinations thereof.

The composition for the topical treatment of a brachycephalic skin condition in a mammal may be topically applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years.

Dosage forms of the composition for the topical treatment of a brachycephalic skin condition in a mammal include, for example, ointments, creams, emulsions, liquids, lotions, gels, aerosols, shampoos, pastes, or foams. Preferably, the composition for the topical treatment of a brachycephalic skin condition in a mammal is a balm that can be easily applied to the skin.

The compositions provided herein may be formulated in a unit dosage form. A unit dosage form refers to a physically discrete unit suitable as a unitary dose for patients undergoing treatment, with each unit containing a predetermined quantity of a composition described herein calculated to produce the intended therapeutic effect. A unit dosage form may be for a single daily dose, 1 to 2 applications per day, or one of multiple daily doses, for example, 2 to 4 applications per day. When multiple daily doses are used, the unit dosage may be the same or different for each dose. One or more dosage forms may comprise a dose, which may be administered to a patient at a single point in time or during a time interval.

The present invention provides a therapeutic kit. The kit includes: a topical composition including: topical treatment of a brachycephalic skin condition in a mammal comprising: about 5 weight percent to about 45 weight percent *Candelilla* wax; about 5 weight percent to about 40 weight percent Shea nut butter; about 5 weight percent to about 25 weight percent Coconut oil; about 1 weight percent to about 20 weight percent hempseed oil; about 1 weight percent to about 20 weight percent *Kukui* nut oil; about 1 weight percent to about 20 weight percent jojoba oil; about 1 weight percent to about 20 weight percent sweet almond oil; about 0.1 weight percent to about 10 weight percent Rosemary extract; about 0.1 weight percent to about 10 weight percent Niaouli oil; and about 0.1 weight percent to about 10 weight percent Vitamin E acetate and instructions for using the topical composition and a dosage regime thereto.

A person skilled in the art will be able to select a container based on the form of the composition and its intended use. For example, an aerosol spray may be supplied in a pressurized can, whereas a lotion may be provided in a plastic bottle. In some embodiments of the kit, an applicator, such as gauze, a tissue, a wipe, a cotton swab or a brush, may also be included.

In addition, a set of instructions is provided. The set of instructions preferably includes information necessary for proper use of the kit, such as dosage and timing of administration of the composition disclosed herein. The set of instruction may comprise instructions on treating skin diseases such as skin folds, skin fold dermatitis, dermatitis, or combinations thereof. A person of ordinary skill in the art will appreciate that the set of instructions can be in any suitable medium, including, without limitation, printed, video-taped, digital, and audio-recorded.

The topical composition may also include, for example, one or more solvents, one or more thickening agents, one or more penetration enhancers, one or more wetting agents, one or more lubricants, one or more emollients, one or more fragrances, one or more pigments, or a combination thereof.

Various methods of making the topical composition are also provided.

Various kits are also provided. Typically, the kits include a topical composition and instructions for using the topical composition and a dosage regime thereto.

The topical compositions, as described herein, may also include one or more optional ingredients, for example, palliative agents, skin conditioning agents, emollients, humectants, odorants, preservatives, solvents, thickening, stiffening and suspending agents, other agents, or a combination thereof.

Typically, the one or more optional ingredients, if present, are present in an amount of about 0.001% to about 30%, about 3% to about 25%, or about 5% to about 15%, by weight. Illustratively, one or more emollients are present in a total amount of about 0.001%, about 0.25%, about 0.5%, about 0.75%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight percent.

Suitable palliative agents include, for example, menthol, camphor, phenol, allantoin, benzocaine, corticosteroids, phenol, zinc oxide, camphor, pramoxine, dimethicone, meradimate, octinoxate, octisalate, oxybenzone, dyclonine, benzyl alcohol, mineral oil, propylene glycol, titanium dioxide, magnesium stearate, and the like, or a combination thereof.

Suitable skin conditioning agents include, for example, mineral oil, petrolatum, dimethicone, dimethicone copolyol, cationic monomers and polymers (such as guar hydroxypropyl trimonium chloride and distearyl dimethyl ammonium chloride), and combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose, and combinations thereof.

Suitable emollients include, for example, caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea, and combinations thereof.

Suitable humectants include, for example, glycerin, propylene glycol, sorbitol, urea, and combinations thereof.

Suitable odorants include, for example, hypoallergenic perfume, menthol, and combinations thereof.

Suitable artificial or man-made preservatives, antioxidants, and chemical stabilizers include, for example, alcohol, benzyl alcohol, butylated hydroxyanisole, butylparaben, calcium acetate, castor oil, chlorocresol, 4-chloro-m-cresol, citric acid, disodium edetate, edetate disodium, ethoxylated alcohol, ethyl alcohol, glycerin, methylparaben, parabens, potassium sorbate, propyl gallate, propylene glycol, propylparaben, sodium bisulfate, sodium citrate, sodium metabisulfite, sorbic acid, tannic acid, triglycerides of saturated fatty acids, zinc stearate, and combinations thereof.

Suitable solvents include, for example, alcohol, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, and SD alcohol 40, triglycerides of saturated fatty acids, and combinations thereof.

Suitable thickening, stiffening and suspending agents include, for example, aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, bentonite, and combinations thereof.

Other optional agents may be added to the composition including, for example, aloe, *arachis* oil, benzoic acid, coenzyme Q10, Q10, dimethicone, *eucalyptus* oil, resorcinol, retinol, retinyl palmitate, retinyl acetate, fennel extract, whey protein, ceramide, silicone, alpha-hydroxy acids, beta-hydroxy acids, sorbitol, vitamin A, vitamin B, vitamin C, vitamin D, Vitamin E, and vitamin K. Unless otherwise indicated, the composition will generally contain less than about 5% by weight and typically less than about 1% by weight of the above-ingredients.

The invention should now be illustrated with the following non-limiting examples. The chemicals were obtained from commercial sources. All chemicals were of reagent grade and distilled and deionized water was used. Unless otherwise indicated, all parts and percentages are by weight and all molecular weights are weight average molecular weight.

EXAMPLES

Example 1

Preparation of the Balm

To a reactor with mixing was added about 20 units of Shea nut butter. The Shea nut butter was slowly heated to about 175° F., held at about 175° F. for about 20 minutes, and the heat was removed. When the temperature had fallen to about 160° F., about 25 units of *candelilla* wax was added and completely mixed in. When the temperature of the composition had dropped to about 110° F., about 15 units of Coconut Oil, about 10 units of Jojoba Oil, about 10 units of Sweet Almond Oil, about 10 units of Hempseed Oil, about 10 units of *Kukui* Nut Oil, about 1 unit of Vitamin E acetate, about 1 unit of Niaouli Oil, and about 1 unit of Rosemary Extract were added with stirring. After the composition was thoroughly mixed, it was poured into containers, placed in a freezer for about 30 minutes, and removed to afford the balm.

Example 2

1½ Year Old Male Bulldog

The folds above dog's nose were red and irritated and had malodor, dog's tear stains were black, had malodor and skin was red with inflammation. Dog had 2 red bumps on two of his paws. Dog had fairly severe interdigital irritation to the point that they bleed. Dog had an infected tail pocket that was malodorous had black crust and was inflamed. To the dog was applied the balm prepared in Example 1 twice/daily after cleaning the problem spots with a baby wipe for 4 days. After 4 days, all the conditions were completely gone.

Example 3

2 Year Old Female Bulldog

Dog was petite in size and overweight. Dog's tail was buried in the tail pocket and was very malodorous, which appeared to be an ongoing yeast infection. Dog also had a patch of missing hair on her side and redness between the toes. To the dog was applied the balm prepared in Example 1 twice/daily after cleaning the problem spots with a baby wipe for 4 days. After 4 days, the dog's hair was growing back, the odor in the tail pocket disappeared, and the redness between her toes was completely been healed.

Example 4

8 Year Old Female Bulldog

Dog had a severely buried tail that was very malodorous and was infected. When her tail pocket was cleaned clumps of black stuff comes out of the pocket. To the dog was applied the balm prepared in Example 1 twice/daily after cleaning the problem spots with a baby wipe for 4 days. After 4 days, the conditions improved.

Example 5

Owner of the above dogs in Examples 2-4 had used Vaseline Petroleum Jelly to treat similar conditions on the dogs, but noticed no improvement. Owner also used Douxo medicated pads twice on the first day and one on the second day, after which the issues resolved themselves.

Examples 6-8

Two bulldogs, age and sex not known, had raw, irritated skin in the folds that dropped down from the inner corner of the eye and were wet from tear production. One bulldog had a reoccurring yeast growth component to the area as well. Applying the formulation from Example 1 once a day, the owner noticed a reduction of the redness and swelling in the fold crease by the 2nd day and, for the one dog, a definite decrease in the yeast and "yeasty odor" by the 3rd day.

Example 9

A male bulldog, age not known, had a very deep fold immediately above the nose, which remained greasy and damp, had considerable debris, and was easily abraded during cleaning. Owner had used several drying and cleaning agents in the past on him with no improvement in condition. The dog's owner applied the balm prepared in Example 1 once per day. A reduction in the "greasiness" and debris was observed by the second day. After 5 days, the dog's considerable fold pocket had no redness, did not become abraded upon cleaning, and had considerably less of the debris, which the dog always had for the previous 5 years. Dog's skin appeared less fragile and was a healthier color. The dog doesn't mind the cleaning and the site does not get red and irritated after cleaning like in the past.

Example 10

A bulldog, age and sex not known, had a very irritated and wide spread, but shallow infected dewlap from a combination of rough housing with other bulldogs and it hanging in the water when he drinks. This is the sort of thing that borders on needing oral antibiotic treatment normally. The dog's owner applied the balm prepared in Example 1 once per day. The irritated area showed a reduction in the accompanying odor by the 2nd day along with a mild reduction of the redness and swelling. After 4 days and the area was healing well. The deeper red sites were still red, but the widespread inflammation was reduced considerably, and the odor has disappeared entirely.

Example 11

Figure 1:
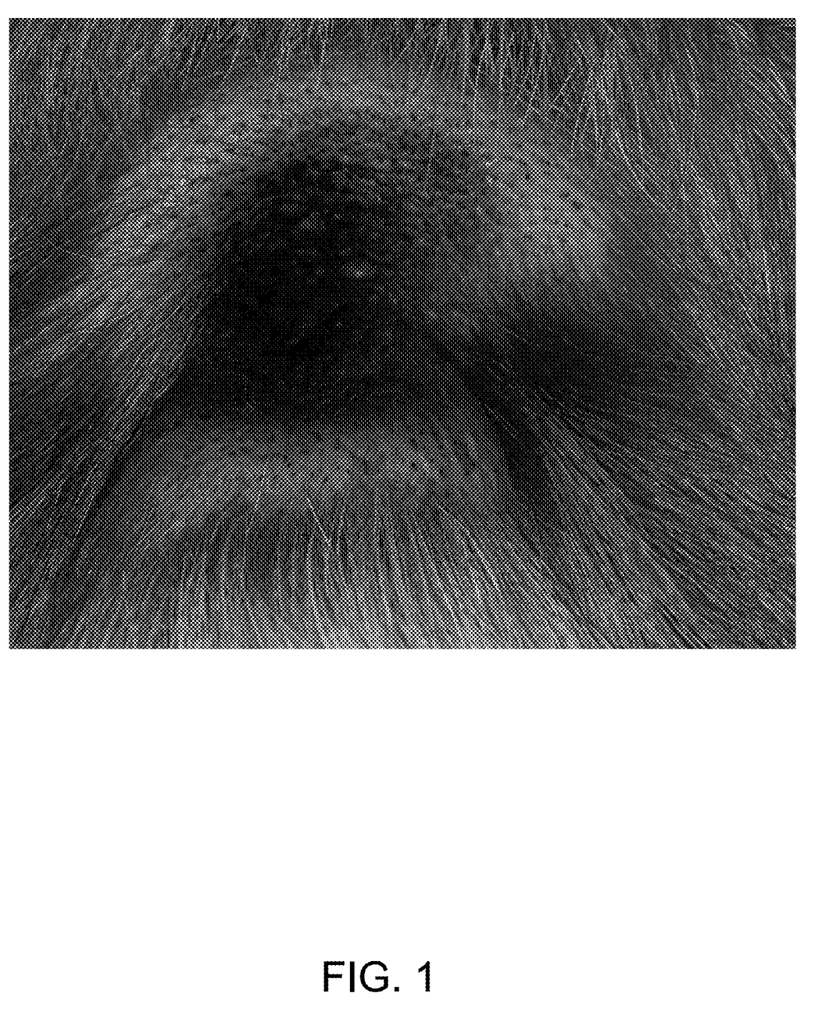
FIG. 1 is a photograph of a dog's ear before treatment.
Figure 2:
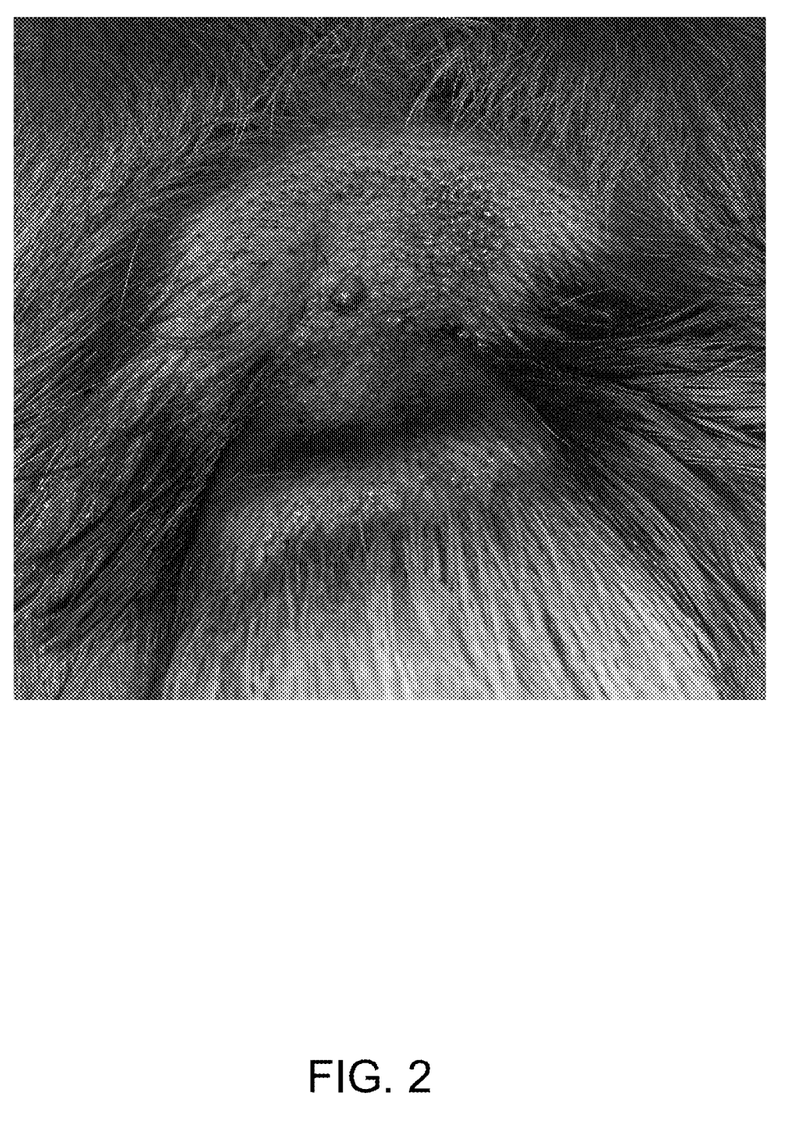
FIG. 2 is a photograph of a dog's ear after treatment.

A 10 year-old male had a deep roll above his tail that extruded a thick tar-like black substance. The dog was bathed to remove some of the black substance before the dog's owner applied the balm prepared in Example 1 twice per day for two days to afford nice pink healthy looking skin. FIG. 1 is a photo of the dog's ear before application of the balm from Example 1. FIG. 2 is a photo of the dog's ear after application of the balm from Example 1 for two days.

Example 12

A male bulldog, age unknown had malodor and interdigital dermatitis. To the dog was applied the balm prepared in Example 1 twice/daily after cleaning the problem spots with a baby wipe for five days. After 5 days, the hair missing on several spots was growing back and the red & inflamed folds on its face had completely cleared up.

Example 13

To a 30-year old obese female human with a skin infection on the skin folds on her abdomen is applied the balm from Example 1 twice pre day until the skin infection recedes.

Example 14

To a 40-year old obese male human with a skin infection on the skin folds on his buttocks is applied the balm from Example 1 twice pre day until the skin infection recedes.

Example 15

Preparation of the Balm

To a reactor with mixing was added about 20 units of Shea nut butter. The Shea nut butter was slowly heated to about 175° F., held at about 175° F. for about 20 minutes, and the heat was removed. When the temperature had fallen to about 150° F., about 25 units of *candelilla* wax was added and completely mixed in. When the temperature of the composition had dropped to about 140° F., about 15 units of Coconut Oil, about 10 units of Jojoba Oil, about 10 units of Sweet Almond Oil, about 10 units of Hempseed Oil, about 10 units of *Kukui* Nut Oil, about 1 unit of Vitamin E acetate, about 1 unit of Niaouli Oil, about 1 unit of grapeseed oil, about 1 unit of olive leaf extract, about 1 unit of *calendula* leaf extract, and about 1 unit of Rosemary Extract were added with stirring. After the composition was thoroughly mixed, it was poured into containers, placed in a freezer for about 30 minutes, and removed to afford the balm.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance or component fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

What is claimed is:

1. A composition for topical treatment of a skin condition in a mammal comprising:
   about 5 weight percent to about 45 weight percent *Candelilla* wax;
   about 5 weight percent to about 40 weight percent Shea nut butter;
   about 5 weight percent to about 25 weight percent Coconut oil;
   about 1 weight percent to about 20 weight percent hempseed oil;
   about 1 weight percent to about 20 weight percent *Kukui* nut oil;
   about 1 weight percent to about 20 weight percent jojoba oil;
   about 1 weight percent to about 20 weight percent sweet almond oil;
   about 0.1 weight percent to about 10 weight percent Rosemary extract;
   about 0.1 weight percent to about 10 weight percent Niaouli oil;
   about 0.1 weight percent to about 10 weight percent grapeseed oil;
   about 0.1 weight percent to about 10 weight percent olive leaf extract;
   about 0.1 weight percent to about 10 weight percent *calendula* leaf extract; and
   about 0.1 weight percent to about 10 weight percent Vitamin E acetate.

2. The composition of claim 1, wherein the skin condition is a intertrigo, a skin fold, skin fold dermatitis, interdigital dermatitis, facial fold dermatitis, vulvar fold dermatitis, tail fold pyoderma and dermatitis, impetigo, Nasodigital hyperkeratosis, pruritus, pyoderma, pyotraumatic dermatitis, malodor, lesions, dermal rashes, dermal bacterial infection, dermal fungal infection, dermal weeping; hot spots, irritation, chaffing, itching; inflammation, or a combination thereof.

3. The composition of claim 1, wherein the mammal comprises a human, canine, a feline, or a rabbit.

4. The composition of claim 1, wherein the composition is a solution, a spray, a lotion, a gel, a cream, a balm, a paste, or an ointment.

5. The composition of claim 1, further comprising one or more vitamins, one or more herbs, one or more antimicrobial agents, one or more anti-inflammatory agents, one or more non-steroidal cosmetic soothing agents, one or more skin lightening agents; one or more anti-wrinkle agents, one or more anti-itching agents, one or more antioxidants, one or more preservatives, one or more fragrances, one or more conditioners, or a combination thereof.

6. A composition for topical treatment of skin fold dermatitis in a canine consisting essentially of:
   about 5 weight percent to about 45 weight percent *Candelilla* wax;
   about 5 weight percent to about 40 weight percent Shea nut butter;
   about 5 weight percent to about 25 weight percent Coconut oil;
   about 1 weight percent to about 20 weight percent hempseed oil;
   about 1 weight percent to about 20 weight percent *Kukui* nut oil;
   about 1 weight percent to about 20 weight percent jojoba oil;
   about 1 weight percent to about 20 weight percent sweet almond oil;
   about 0.1 weight percent to about 10 weight percent Rosemary extract;
   about 0.1 weight percent to about 10 weight percent Niaouli oil;
   about 0.1 weight percent to about 10 weight percent grapeseed oil;
   about 0.1 weight percent to about 10 weight percent olive leaf extract;
   about 0.1 weight percent to about 10 weight percent *calendula* leaf extract; and
   about 0.1 weight percent to about 10 weight percent Vitamin E acetate.

7. The composition of claim 6, wherein the composition is a solution, a spray, a lotion, a get, a cream, a balm, a paste, or an ointment.

8. The composition of claim 7, wherein the composition is a balm.

9. A method of topically treating skin fold dermatitis in a canine comprising: administering a composition consisting essentially of;
   about 5 weight percent to about 45 weight percent *Candelilla* wax;
   about 5 weight percent to about 40 weight percent Shea nut butter;
   about 5 weight percent to about 25 weight percent Coconut oil;
   about 1 weight percent to about 20 weight percent hempseed oil;
   about 1 weight percent to about 20 weight percent *Kukui* nut oil;
   about 1 weight percent to about 20 weight percent jojoba oil;
   about 1 weight percent to about 20 weight percent sweet almond oil;
   about 0.1 weight percent to about 10 weight percent Rosemary extract;
   about 0.1 weight percent to about 10 weight percent Niaouli oil;

about 0.1 weight percent to about 10 weight percent grapeseed oil;

about 0.1 weight percent to about 10 weight percent olive leaf extract;

about 0.1 weight percent to about 10 weight percent *calendula* leaf extract; and about 0.1 weight percent to about 10 weight percent Vitamin E acetate, to an area of skin fold dermatitis in the canine to be treated.

10. The method of claim 9, wherein the composition is a solution, a spray, a lotion, a gel, a cream, a balm, a paste, or an ointment.

11. The method of claim 10, wherein the composition is a balm.

\* \* \* \* \*